United States Patent [19]

Tomuro et al.

[11] Patent Number: 4,736,060

[45] Date of Patent: Apr. 5, 1988

[54] METHOD FOR OPTICAL RESOLUTION OF DL-CYSTEINE AND (R,S)-1-(1-NAPHTHYL) ETHYLAMINE

[75] Inventors: Keizō Tomuro, Urawa; Yoshiharu Tamura, Tokyo; Yoko Morimoto, Tokyo; Shigeyoshi Katoh, Tokyo, all of Japan

[73] Assignee: Nippon Rikagakuyakuhin Co., Ltd., Tokyo, Japan

[21] Appl. No.: 892,059

[22] Filed: Aug. 1, 1986

[30] Foreign Application Priority Data

Aug. 6, 1985 [JP] Japan .................. 60-171894
Sep. 19, 1985 [JP] Japan .................. 60-205343

[51] Int. Cl.$^4$ ............................. C07B 57/00
[52] U.S. Cl. ..................... 562/401; 562/557; 548/201; 564/304
[58] Field of Search ............. 562/401, 557; 564/304

[56] References Cited

U.S. PATENT DOCUMENTS

| | | | |
|---|---|---|---|
| 3,000,947 | 9/1961 | Bottoms | 564/304 |
| 3,679,694 | 7/1972 | Rambacher et al. | 562/401 X |
| 3,808,268 | 4/1974 | Rambacher et al. | 562/401 |
| 4,416,828 | 11/1983 | Bethge et al. | 260/501.12 |
| 4,430,509 | 2/1984 | Bethge et al. | 562/401 |
| 4,613,688 | 9/1986 | Inoue et al. | 562/401 |
| 4,621,151 | 11/1986 | Nohira et al. | 562/401 |

Primary Examiner—Werren B. Lone
Assistant Examiner—Vera C. Clarke
Attorney, Agent, or Firm—Murray and Whisenhunt

[57] ABSTRACT

Method for optical resolution of DL-cysteine by (1) reacting DL-cysteine with formaldehyde to prepare DL-thiazolidine-4-carboxylic acid (DL-TCA), (2) forming diastereomer salts of D-TCA and of L-TCA by reacting DL-TCA with an optically active 1-(1-naphthyl)ethylamine, (3) separating said diastereomer salts by difference of the solubilities thereof in a solvent, (4) recovering D-TCA from said diastereomer salt of D-TCA and finally obtain D-cysteine, and recovering L-TCA from said diastereomer salt of L-TCA and finally obtain L-cysteine.

Method for optical resolution of (R,S)-1-(1-naphthyl)ethylamine (R,S)-NEA by (1) reacting an optically active cysteine with formaldehyde to prepare an optically active thiazolidine-4-carboxylic acid, (2) forming diastereomer salts of (R)-NEA and of (S)-NEA by reacting (R,S)-NEA with optically active thiazolidine-4-carboxylic acid, (3) separating said diastereomer salts of (R)-NEA and of (S)-NEA by difference of the solubilities thereof in a solvent, (4) recovering (R)-NEA from said diastereomer salt of (R)-NEA, and recovering (S)-NEA from said diastereomer salt of (S)-NEA.

4 Claims, No Drawings

METHOD FOR OPTICAL RESOLUTION OF DL-CYSTEINE AND (R,S)-1-(1-NAPHTHYL) ETHYLAMINE

FIELD OF THE INVENTION

The present invention relates to a method for optical resolution of DL-cysteine and (R,S)-1-(1-naphthyl)ethylamine.

Both L-cysteine and D-cysteine are important compounds, since they are used widely for various pharmaceutical products, cosmetics and for food additives. Recently, L-cysteine is produced mainly from the natural resources through extraction method. However, availability of the natural resources is limited, increasing demand of L-cysteine cannot be satisfied. Similar to the above, a large quantity of demand of D-cysteine is expected as for intermediates of synthesizing various antibiotics, however D-cysteine is produced only by method of optical resolution of DL-cysteine, any suitable method for producing D-cysteine in an industrial scale have not been developed yet.

Under the circumstances, optical resolution method for DL-cysteine which can be suitable for industrial scale application is greatly desired, since DL-cysteine can be produced in a large scale with less expensive production cost through synthetic methods. [Japanese Patent Publication No. 58-5194 (1983), Japanese Patent Publication No. 57-16099 (1982) and Angew. Chem., (1981), Vol. 93, page 45].

On the other hand, (R,S)-1-(1-naphthyl)ethylamine is widely used for optical resolving agent, similar to natural basic optical resolving agents, such as ephedrine, quinine and the like, again optical resolution method for (R,S)-1-(1-naphthyl)ethylamine is greatly desired.

PRIOR ART

1. There are known some methods for optical resolution of DL-cysteine in prior art literatures as follows:

(1) Methods using enzymes:

(1) Method of treating S-benzyl-N-acetyl-DL-cysteine with aminoacylase. [Arch. Biochem. Biophys., Vol., 39, page 108 (1952)].

(2) Method of treating S-benzyl-DL-cysteine with amides. [J. Bio. Chem., Vol. 184, page 55, (1950)].

(3) Method of treating S-alkylmercapto-N-acetyl-DL-cysteine. [Japanese Patent Publication No. 57-21985 (1982)].

(2) Methods for converting DL-cysteine into diasteromers by using optical resolving agent having optical activity:

(1) Method of treating S-benzyl-N-formyl-DL-cysteine with brucine. [J. Bio. Chem., Vol. 130, page 109, (1939)].

(2) Method of treating DL-cysteine with mandelic acid. [Japanese Patent Application Kokai (Laid-open) No. 57-193448 (1982)].

(3) Method for optical resolution of 2-substituted-thiazolidine-4-carboxylic acid prepared by reacting DL-cysteine with an optically active sugar. [Japanese Patent Publication No. 60-33824 (1985)].

(3) Methods of preferential crystallization:

(1) Method of preferential crystallization of DL-cysteine hydrochloride. [Japanese Patent Publication No. 60-55063 (1985)].

(2) Method of preferential crystallization of DL-thiazolidine-4-carboxylic acid. [Japanese Patent Application Kokai (Laid-open) No. 60-142952 (1985)].

These methods known in the prior art literatures, however are not considered as satisfactory methods for optical resolution of DL-cysteine which can be applied for industrial scale production, for the reasons that these methods involve several difficulties, such as lower yield of the desired products, complexity in the process steps, difficulties on controlling the optical resolution conditions and others.

2. On the other hand, methods for optical resolution of (R,S)-1-(1-naphthyl)ethylamine are reported in the prior art literatures as follows:

(1) Method by using (+)-tartaric acid. [U.S. Pat. No. 2,996,545 (1961) by R. R. Bottoms].

(2) Method by using (−)-menthylphthalate. [U.S. Pat. No. 3,000,947 (1961) by R. R. Bottoms].

(3) Method by using (−)-di-O-isopropylidene-2-keto-L-gulonic acid. [U.S. Pat. No. 3,904,632 (1975) by C. William].

(4) Method of using cis-1,2-cyclohexanedicarboxylic acid. [Japanese Patent Application Kokai (Laid-open) No. 57-146743 (1982)].

(5) Method by using cis-2-benzamidocyclohexanecarboxylic acid. [Japanese Patent Application Kokai (Laid-open) No. 58-24545 (1983)].

These methods known in the prior art literatures, however are not considered as satisfactory methods for optical resolution of (R,S)-1-(1-naphthyl)ethylamine which can be applied for industrial scale production, for the reasons that these methods require a large quantity of organic solvents, and can only be obtained the desired optically active products having high purity in lower yield since several steps of recrystallization are required.

SUMMARY OF THE INVENTION

An object of the present invention is to provide a method for optical resolution of DL-cysteine so as to obtain D-cysteine and L-cysteine having high optical purity in high yields.

Another object of the present invention is to provide a method for optical resolution of (R,S)-1-(1-naphthyl)ethylamine so as to obtain (R)-1-(1-naphthyl)ethylamine and (S)-1-(1-naphthyl)ethylamine, both of which having high optical purity, in high yields.

DETAILED EXPLANATION OF THE INVENTION

The present inventors have conducted extensive studies for overcoming several drawbacks involved in the methods known in the prior art literatures, and finally succeeded to establish the present invention by using thiazolidine-4-carboxylic acid (hereinafter referred to as "TCA", thus optically inactive isomer is referred to as "DL-TCA", and optically active isomers are referred to as "D-TCA" and "L-TCA", respectively) having the formula:

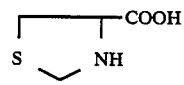

for optical resolution of DL-cysteine to obtain D-cysteine and L-cysteine, as well as for optical resolution of (R,S)-1-(1-naphthyl)ethylamine [hereinafter referred to as "(R,S)-NEA", and optically active isomers are referred to as "(R)-NEA" and "(S)-NEA", respectively].

Generally, the mercapto group in cysteine is a functional group having highly reactivity which is susceptible to oxidation, for this reason when optical resolution of cysteine is conducted without protecting the mercapto group, the resultant optically active isomers can only be obtained in lower yields and with lower optical purities. Furthermore, cysteine in which the mercapto group is protected, can hardly form a NEA-salt thereof in a solvent, if the amino group therein is also protected, similar to in the case of neutral amino acids.

The TCA used in the present invention has the structural formula in which the mercapto group and the amino group in the cysteine are protected at the same time, thus optically inactive isomer and optically active isomers can be obtained in higher yield when each of the corresponding optical isomers of cysteine is reacted with formaldehyde in water [J. Amer. Chem. Soc., Vol. 59, page 200 (1937)].

This TCA can easily be formed a salt with NEA in a solvent. Also TCA opens its ring structure to forms cystine which is a dimer of cysteine when it is treated with an oxidizing agent such as hydrogen peroxide, iodine or the like, in an aqueous medium [J. Amer. Chem. Soc., Vol. 59, page 200, (1937)].

Cystine can be converted into cysteine by a common reducing method, for example electrolytic reduction [Japanese Patent Application Kokai (Laid-open) No. 51-136620 (1976)]. Thus, optically active isomers of TCA obtained from optical resolution of DL-TCA can easily be converted into the corresponding optically active isomers of cysteines.

The present invention is characterized by treating DL-TCA with an optically active NEA isomer [(R)-NEA or (S)-NEA] to form a corresponding diasteromer salt, then separating said diasteromer salt by the difference of solubility in the solvent, or by treating (R,S)-NEA with an optically active TCA isomer (D-TCA or L-TCA) to form a corresponding diasteromer salt, then separating said diasteromer salt by the difference of solubility in the solvent.

In conducting an optical resolution according to the present invention, any one of the optically resolving agent, i.e., (R)-NEA, (S)-NEA, or D-TCA, L-TCA is dissolved in a suitable solvent, by warming, with DL-TCA or (R,S)-NEA, respectively, then the thus prepared solution is cooled slowly to a predetermined temperature, and allowed to stand for a certain hours, so as to preferentially crystallize any one of the two diasteromers formed in the solution. The crystals thus precipitated in the solution is collected by means of, for example, filtration, and the mother liquor is further cooled to a certain temperature and allowed to stand for a certain length of time, then another diasteromer salt is crystalized.

As to the solvent to be used in the present method, water or any organic solvents, such as methanol, ethanol, 1-propanol, 2-propanol, 1-butanol, 2-butanol and acetone and the like can be used in single form or a mixture thereof, and from an industrial purpose, water is used preferably.

The amount of the solvent to be used in the present method, there are some differences between the type of the solvents, and generally a certain times of the solvent to the amount of the salt formed can be used, and there is not any restriction to the amount of the solvent. Preferably, when water is used, which is advantageous from an industrial standpoint, generally 1.0 to 5.0 times of water is preferably used.

The cooling temperature for crystallizing the hardly soluble salts is different depend on the type of the solvent and the amount of the solvent used, and generally a temperature in the range of from 10° C. to 50° C. can be applied, and in view of the easiness in practical operation, room temperature is the most preferable. In addition to the above, the temperature for crystallizing another salt of diasteromer, a temperature in the range of from 0° C. to −20° C. is preferable.

The time for stand the solution to crystallize the salt is not specifically restricted, and can be selected from a wide range, and generally, 10 to 24 hours is preferable for crystallize the salt sufficiently with make the operation efficiently.

The molar ratio of the optical resolving agent to the optically inactive isomer to be optically resolved is not specifically restricted, and can be selected from a wide range, and generally an equimolar quantity of both optical resolving agent and optically inactive isomer can be used preferably.

Next, an aqueous solution of sodium hydroxide or of potassium hydroxide is added to the salt, the salt is decomposed and NEA is separated as an oily substance. Then, said oily substance is extracted with an organic solvent, the TCA is separated in the aqueous layer, and the NEA is separated in the organic layer.

As to the organic solvent used for the extraction, any organic solvent which will not miscible with water, and can be able to dissolve the NEA can be used. In view of to make the extraction efficiently, diethyl ether, diisopropyl ether and ethyl acetate and the like may preferably be used.

According to method of the present invention, in the case of optical resolution of DL-TCA by using (R)-NEA, after the treatment of firstly crystallized salt, to the aqueous solution being separated is added hydrochloric acid so as to adjust the pH to about 4.0, then the solution is concentrated and cooled to obtain D-TCA having high optical purity can be obtained as crystals. On the other hand, another salt obtained by cooling further lower temperature, there can be obtained L-TCA having high optical purity can be obtained by treating similarly to that in the case of the salt firstly obtained. In this case, to the filtrate obtained after separation of the first salt, is added a predetermined amount of an aqueous solution of sodium hydroxide or of potassium hydroxide so as to separate (R)-NEA as in the form of an oily substance, and after said oily substance is removed by extraction with an organic solvent, hydrochloric acid is added to the aqueous solution to adjust the pH to about 4.0, then the solution is concentrated and cooled to obtain L TCA having high optical purity can also be obtained. The (R)-NEA being extracted with the organic solvent can be recovered in higher yield by removing the organic solvent.

In the case of conducting optical resolution of DL-TCA by using (S)-NEA as the optical resolving agent, L-TCA can be obtained from the firstly crystallized salt on one hand, and D-TCA can be obtained from the filtrate after separation of the firstly formed salt, or can be obtained the salt precipitated at lower cooled temperature on the other hand.

While, in accordance with the present invention, in the case of conducting optical resolution of (R,S)-NEA by using L-TCA as the optical resolving agent, the salt firstly crystallized is treated by a procedure similar to the above, then the organic solvent layer is dehydrated with anhydrous sodium sulfate, then the dehydrating agent is removed by filtration, the organic solvent is removed by evaporation under reduced pressure, if necessary the desired product can be obtained by distillation, so that (S)-NEA having high optical purity can be obtained, on one hand. The crystals precipitated lower temperature are treated by a method similar to that used in the firstly obtained salt, then (R)-NEA can be obtained. In this case, to the filtrate being separated the firstly crystallized salt by filteration is made alkaline, then removed NEA containing much amount of (R)-isomer, and further conducting optical resolution by using D-TCA, there is obtained (R)-NEA in a high yield.

In the case of conducting optical resolution of (R,S)-NEA by using D-TCA, similar to the above, (R)-NEA can be obtained from the firstly crystallized salt on one hand, and (S)-NEA can be obtained from the salt crystallized at lower temperature on the other hand.

The present invention relates to optical resolution of (R,S)-NEA by using optically active TCA, or to optical resolution of DL-TCA by using optically active NEA. However, when the method is conducting practically, it is preferable to carry out optical resolution of (R,S)-NEA by using L-TCA which is the only obtainable optical isomer prepared from L-cysteine exists in the natural resource.

Thus, in the case of optically resolving (R,S)-NEA by using L-TCA, there can be obtained (S)-NEA and (R)-NEA. Then DL-TCA is optically resolved by using (R)-NEA or (S)-NEA, then L-TCA and D-TCA can be obtained. As explained above, the optically active isomers once obtained according to the present invention, they can be recovered in high yield, and thus said optically active isomers can be used repeatedly for obtaining the desired optical isomers.

The present invention can be explained by way of illustrating the following examples, however, the present invention is not restricted only to these examples.

EXAMPLE 1

To 500 ml of water, there was added 171.2 g (1 mol) of (R,S)-NEA and 133.3 g (1 mol) of L-TCA, then the whole mixture was heated to 80°–90° C. with stirring on a water-bath so as to dissolve the solid matters. Heating was stopped when the solid matters were completely dissolved, (S)-NEA.L-TCA was added as the crystal nucleus, and the solution was cooled to 20° C. and allowed to stand for 24 hours. The crystals precipitated were collected by filtration and dried, there was obtained 125 g of (S)-NEA.L-TCA salt.

To 125 g of the above-mentioned crystals, there was added 500 ml of 1N-sodium hydroxide aqueous solution, then the oily substance separated therefrom was extracted twice with 500 ml of diethyl ether. The ether layer was dehydrated with anhydrous sodium sulfate, and diethyl ether was removed by evaporation under reduced pressure, there was obtained 70 g of (S)-NEA (yield: 40.9%). ]$\alpha]_D^{20} = -60.1°$ (c=2 methanol). Optical purity=96.9%.

To the filtrate after separation of the salt which is hardly soluble in water, there was added (R)-NEA.L-TCA as the crystal nucleus, then was cooled to $-5°$ C., and allowed to stand for 24 hours. Then the crystals precipitated were collected by filtration and dried, there was obtained 86 g of salt of (R)-NEA.L-TCA.

To 86 g of the crystals, there was added 300 ml of 1N-sodium hydroxide aqueous solution, then the oily substance separated therefrom was extracted twice with 300 ml of diethyl ether. The ether layer was dehydrated with anhydrous sodium sulfate, and diethyl ether was removed by evaporation under reduced pressure, there was obtained 44.5 g of (R)-NEA (yield=26%). $[\alpha]_D^{20} = +60.9°$, (c=2 methanol). Optical purity 98.2%.

EXAMPLE 2

To 500 ml of water, there were added 171.2 g (1 mol) of (R,S)-NEA and 133.3 g (1 mol) of L-TCA, then the whole mixture was heated to 80°–90° C. with stirring on a water-bath so as to dissolve the solid matters. Heating was stopped when the solid matters were completely dissolved, (S)-NEA.L-TCA was added as the crystal nucleus, and the solution was cooled to 20° C. and allowed to stand for 24 hours. The crystals precipitated were collected by filtration, and dried, there was obtained 128 g of (S)-NEA.L-TCA.

To 128 g of the crystals, there was added 500 ml of 1N-sodium hydroxide aqueous solution, then the oily substance separated therefrom was extracted twice with 500 ml of diethyl ether. The ether layer was dried with anhydrous sodium sulfate, and diethyl ether was removed by evaporation under reduced pressure, there was obtained 71 g of (S)-NEA (yield: 41.5%), $[\alpha]_D^{20} = -59.9°$ C. (c=2 methanol), Optical purity: 96.9%.

To the filtrate after separation of the salt which is hardly soluble in water, there was added 130 ml of 5N-sodium hydroxide aqueous solution, then the oily substance separated thereform was extracted twice with 200 ml of diethyl ether. The ether layer was dehydrated with anhydrous sodium sulfate, and diethyl ether was removed by evaporation under reduced pressure, there was obtained 98 g (yield=57.8%) of NEA containing (R)-isomer in much amount. $[\alpha]_D^{20} = +40.9°$ (c=2 methanol)

Two of aqueous layers after extraction of NEA were combined, then 98 ml of concentrated hydrochloric acid was added thereto so as to adjust the pH to about 4, then this mixture was concentrated under pressure so as to the volume of about 400 ml. The resultant concentrate was allowed to stand in a refrigerator for 24 hours. The crystals thus formed were collected by filtration, and dried. There was obtained 125 g of L-TCA (recovery rate: 93.8%) $[\alpha]_D^{20} = -206.3°$ (c=4 1N-NaOH).

EXAMPLE 3

To 25 ml of water, there were added 6.66 g ($5 \times 10^{-2}$ mol) of DL-TCA and 8.56 g ($5 \times 10^{-2}$ mol) of (S)-NEA obtained in Example 1, then the mixture was heated to 80°–90° C. with stirring on a water-bath. Heating was stopped when the solid matters were completely dissolved, the mixture was cooled slowly to 20° C., then allowed to stand as it was for 24 hours. The crystals precipitated were collected by filtration, and dried to obtain 6.4 g of L-TCA-(S)-NEA salt.

50 Milliliters of 0.5N-sodium hydroxide aqueous solution was added to the above-mentioned crystals, then the oily substance separated therefrom was extracted twice with 50 ml of diethyl ether. To the aqueous layer was added hydrochloric acid so as to adjust the pH of the solution to about pH 4, then was concentrated the aqueous layer under reduced pressure to dryness, then 20 ml of water was added to the residue. Then the resultant solution was allowed to stand in a refrigerator for about 24 hours. The crystals precipitated were collected by filtration and dried. There was obtained 2.4 g of L-TCA (yield=36%). $[\alpha]_D^{20} = -207.1°$ (c=4 1N-NaOH).

To the filtrate after separation of the salt which is hardly soluble in water, there was added D-TCA.(S)-NEA as the crystal nucleus, then the mixture was cooled to −5° C., and allowed to stand as it was for 24 hours. The crystals thus precipitated were collected by filtration to obtain 4.5 g of D-TCA-(S)-NEA salt.

40 Milliliters of 0.5N-sodium hydroxide aqueous solution was added to 4.5 g of D-TCA.(S)-NEA salt, then the oily substance separated therefrom was extracted twice with 40 ml of diethyl ether. To the aqueous layer was added hydrochloric acid so as to adjust the pH to about 4, then water was removed by evaporation to remove about 15 ml of water. Thus obtained concentrate was allowed to stand in a refrigerators for 24 hours. The crystals precipitated were collected by filtration and dried, there was obtained 1.5 g (yield=22.5%) of D-TCA. $[\alpha]_D^{20} = +206.3°$ (c=4 1N-NaOH).

EXAMPLE 4

340 Milliliters of water was added to 98 g ($5.72 \times 10^{-1}$ mol) of NEA containing much amount of (R)-isomer prepared in the above-mentioned Example 2 and 76.3 g ($5.72 \times 10^{-1}$ mol) of D-TCA prepared in the above-mentioned Example 3, the mixture was heated with stirring on a water bath so as to dissolve the solid matters. Heating was stopped when the solid matters were dissolved completely. The solution was cooled slowly to 20° C., and allowed to stand as it was for 24 hours. The crystals precipitated were collected by filtration to obtain 125 g of (R)-NEA.D-TCA salt.

To this crystals was added 500 ml of 1N-sodium hydroxide aqueous solution, then the oily substance separated therefrom was extracted twice with 500 ml of diethyl ether. The ether layer was dried with anhydrous sodium sulfate, then this drying agent was removed by filtration, and diethyl ether was removed by evaporation under pressure. There was obtained 68 g (yield=39.7%) OF (R)-NEA. $[\alpha]_D^{20} = +61.4°$ (c=2 methanol). Optical purity=99.0%.

EXAMPLE 5

To 25 ml of water was added 8.56 g ($5 \times 10^{-2}$ mol) of (R,S)-NEA and 6.66 g ($5 \times 10^{-2}$ mol) of D-TCA, then the mixture was heated to 80°–90° C. with stirring on a water-bath so as to dissolve the solid matters. Heating was stopped when the solid matters were completedly dissolved. The solution was cooled slowly to 20° C., and allowed to stand as it was for 24 hours. The crystals precipitated were collected by filtration and dried, there was obtained 6.1 g of (R)-NEA.D-TCA salt.

The crystals were recrystallized from 20 ml of water to obtain 5.4 g of (R)-NEA.D-TCA salt.

To the said crystals was added 50 ml of 0.5N-sodium hydroxide aqueous solution, then the oily substance separated therefrom was extracted twice with 50 ml of diethyl ether. The ether layer was dried with anhydrous sodium sulfate, and the drying agent was removed by filtration, then diethyl ether was removed by evaporation under reduced pressure to obtain 3.0 g of (R)-NEA (yield 35%). $[\alpha]_D^{20} = -62.0°$ (c=2 methanol). Optical purity 100%.

EXAMPLE 6

To 30 ml of water was added 6.66 g ($5 \times 10^{-2}$ mol) of DL-TCA and 8.56 g ($5 \times 10^{-2}$ mol of (R)-NEA, and the mixture was heated with stirring to 80°–90° C. on a water-bath so as to dissolve the solid matters. Heating was stopped when the solid matters were completely dissolved. The solution was cooled slowly to 10° C., and allowed to stand as it was for 24 hours. The crystals precipitated were collected by filtration and dried, there was obtained 6.5 g of D-TCA.(R)-NEA salt.

The above-mentioned crystals were dissolved in 50 ml of 0.5N-sodium hydroxide aqueous solution, then the oily substance separated therefrom was extracted twice with 50 ml of diethyl ether. To the aqueous layer was added concentrated hydrochloric acid so as to adjust the pH of the solution to about 4, and was concentrated under reduced pressure, to dryness, then 20 ml of water was added to the resultant residue and this solution was allowed to stand in a refrigerator for overnight. The crystals precipitated were collected by filtration, and dried to obtain 2.5 g (yield=37.9%) of D-TCA. $[\alpha]_D^{20} = +207.2°$ (c=4 1N-NaOH).

1.33 g of D-TCA was dissolved in 90 ml of water, then 0.5 ml of 35% hydrogen peroxide was added, and the mixture was allowed to stand in a refrigerator overnight. The crystals precipitated were collected by filtration, and dried to obtain 1.0 g of D-cystine (yield=83.3%). $[\alpha]_D^{20} = +223.5°$. (c=2 1N-HCl).

To the filtrate after separation of the hardly soluble D-TCA.(R)-NEA salt was added 15 ml of 2N-sodium hydroxide aqueous solution, then the oily substance separated therefrom was extracted twice with 50 ml of diethyl ether. To the aqueous layer was added concentrated hydrochloric acid to adjust the pH of the solution to about pH 4, then the aqueous solution was concentrated under reduced pressure to remove dryness, then 20 ml of water was added to the residue. The resultant solution was allowed to stand in a refregirator overnight. The crystals precipitated were collected by filtration, and dried to obtain 2.5 g of L-TCA (yield=37.9%). $[\alpha]_D^{20} = -206.9°$ (c=4 1N-NaOH).

1.33 of L-TCA was dissolved in 90 ml of water, and 0.51 ml of 35% hydrogen peroxide was added, then the mixture was allowed to stand in a refrigerator overnight. The crystals precipitated were collected by filtration and dried. There was obtained 1.0 g of L-cystine (yield=83.3%). $[\alpha]_D^{20} = -222.1°$ (c=1 1N-HCl).

EXAMPLE 7

To 120 g of D-cystine, obtained by a method similar to that described in Example 6, added 120 ml of concentrated hydrochloric acid and 300 ml of water. This solution was used as the negative electrode solution. On the other hand, an aqueous solution prepared by diluting 7.5 ml of concentrated sulfuric acid with 75 ml of water, was used as the positive electrode solution. As to the diaphragm, Selemion CMV cationic ion-exchange membrane (manufactured by Asahi Glass Co., Ltd.) was used, further a silver plate was used as the negative electrode and platinum plate was used as the positive electrode. Electrolytic reduction was conducted at 7–8 A of current, and 4.5–5 volts for 15 hours. After the electrolytic reduction was completed, the negative electrode solution was taken out, and decolored by adding 3 g of activated carbon with stirring. Then the activated carbon was removed by filtration and the resulting filtrate was concentrated under pressure and the crystals were precipitated. The crystals were collected by filtration and dried to obtain 165.5 g of D cysteine hydrochloride monohydrate. (yield: 94%). $[\alpha]_D^{20} = -6.31°$ (c=8 1N-HCl).

EXAMPLE 8

By a method similar to that described in Example 7, there was obtained 158 g (yield=89.5%) of L-cysteine hydrochloride monohydrate was obtained from 120 g of L-cystine prepared by a method similar to that described in Example 6. $[\alpha]_D^{20} = +6.28°$ (c=8 1N-HCl).

What is claimed is:

1. A method for optical resolution of DL-cysteine comprising:
    (1) reacting DL-cysteine with formaldehyde to prepare DL-thiazolidine-4-carboxylic acid (DL-TCA);
    (2) reacting said DL-TCA with an optically active 1-napthylethylamine to form disastereomer salts of D-thiazolidine-4-carboxylic acid (D-TCA) and of L-thiazolidine-4-carboxylic acid (L-TCA);
    (3) separating said diastereomer salts of D-TCA and of L-TCA by difference of the solubilities thereof in a solvent;
    (4) decomposing said diastereomer salt of D-TCA to liberate D-TCA and recovering said D-TCA;
    (5) decomposing said diastereomer salt of L-TCA to liberate L-TCA and recovering said L-TCA;
    (6) converting said D-TCA to D-cysteine and recovering said D-cysteine;
    (7) converting said L-TCA to L-cysteine and recovering said L-cysteine.

2. The method according to claim 1, wherein the optically active 1-naphthylethylamine is selected from the group consisting of (R)-1-(1-naphthyl)ethylamine and (S)-1-(1-naphthyl)ethylamine.

3. A method for optical resolution of (R,S)-1-(1-naphthyl)ethylamine ((R,S)-NEA) comprising:
    (1) reacting an optically active cysteine with formaldehyde to prepare an optically active thiazolidine-4-carboxylic acid;
    (2) reacting (R,S)-NEA with said optically active thiazolidine-4-carboxylic acid to form diastereomer salts of (R)-1-(1-naphthyl)ethylamine ((R)-NEA) and of (S)-1-(1-naphthyl)ethylamine ((S)-NEA);
    (3) separating said diastereomer salts of (R)-NEA and (S)-NEA by difference of the solubilities thereof in a solvent;
    (4) decomposing said diastereomer salt of (R)-NEA to liberate (R)-NEA and recovering said (R)-NEA;
    (5) decomposing said diastereomer salt of (S)-NEA to liberate (S)-NEA and recovering said (S)-NEA.

4. The method according to claim 3, wherein said optically active thiazolidine-4-carboxylic acid is D-thiazolidine-4-carboxylic acid (D-TCA) or L-thiazolidine-4-carboxylic acid (L-TCA).

* * * * *